United States Patent [19]

Kuroda

[11] Patent Number: 5,176,646
[45] Date of Patent: Jan. 5, 1993

[54] MOTORIZED SYRINGE PUMP

[76] Inventor: Takayuki Kuroda, c/o Yuasa Shoji Co., Ltd. 13-10, Nihonbashi-odenmacho Chuo-ku, Tokyo, Japan

[21] Appl. No.: 657,637

[22] Filed: Feb. 19, 1991

[51] Int. Cl.⁵ .............................................. A61M 37/00
[52] U.S. Cl. .................................... 604/154; 604/151; 604/131; 128/DIG. 1
[58] Field of Search ............... 604/151, 152, 154, 155, 604/67; 128/DIG. 1, DIG. 12, DIG. 13; 222/333

[56] References Cited

U.S. PATENT DOCUMENTS

| | | | |
|---|---|---|---|
| 3,279,653 | 10/1966 | Pfleger | 222/333 X |
| 3,931,915 | 1/1976 | Downings et al. | 222/333 X |
| 4,627,835 | 12/1986 | Fenton, Jr. | 128/DIG. 1 X |
| 4,741,732 | 5/1988 | Crankshaw et al. | 604/155 X |
| 5,034,004 | 7/1991 | Crankshaw | 128/DIG. 1 |

FOREIGN PATENT DOCUMENTS 63-190921 12/1988 Japan.

Primary Examiner—John J. Wilson
Assistant Examiner—Jeffrey A. Smith

[57] ABSTRACT

A syringe pump in which a movable member is attached to a frame so as to be movable forward and backward, a transmission roller, transmission gear and speed increasing gear are attached to the movable member, the drive force of a motor is transmitted to the transmission roller through a timing belt, and a clutch mechanism including a rotating member with teeth and a rotation preventing member with teeth engaged with the former teeth is provided whereby the drive force of the transmission gear is transmitted to the rotating member through a guide member comprising a timing belt. The movable member moves along the guide member in the state where the teeth of the rotating member and rotation preventing member are engaged with each other.

1 Claim, 12 Drawing Sheets

MOTORIZED SYRINGE PUMP

BACKGROUND OF THE INVENTION

1. Field of the Invention

The present invention relates to syringe pumps which discharge a small quantity of liquid using a syringe which includes a cylindrical casing and a piston enclosed therein and used as a liquid discharge unit in a medical device or an industrial device.

2. Description of the Related Art

Recently, demands for discharging a small quantity of liquid arise in various fields of industries, for example, a demand for administering a carcinostatic substance dropwise in the field of medical cares over a long time and a demand for discharging a minimum required quantity of soldering paste to a welded point in the field of electronic part manufacture. Generally, a liquid such as a carcinostatic substance to be discharged is exchanged in accordance with application and easy exchange of such liquid is required. In the past, a syringe pump is used to discharge a liquid accurately and to facilitate the exchange of that liquid.

FIG. 12 shows a technique related to syringe pumps. Disposed within a box-like frame 50 in FIG. 12 is a guide rod 51 to which a member 52 movable axially of guide rod 51 is attached. Cylindrical casing 71 of syringe 70 is fixed on top of frame 50 by syringe holder 53. Syringe piston 72 is engaged with movable member 52, so that when piston 72 moves forward in accordance with the movement of movable member 52, a liquid is discharged out of cylinder 70. Screw shaft 54 is provided rotatable and parallel to guide rod 51 within frame 50. A pair of half nuts 55 is engaged on screw shaft 54. Upper half nut 55 is connected to rod 56 attached to movable member 52. Drive gear 57 is attached to an end of screw shaft 54 and connected to gear 60 fixed to output shaft 59A of motor 59 through intermediate gear 58. Therefore, when motor 59 is driven, screw shaft 54 is rotated through gears 57, 58 and 60, so that half nuts 55 and movable member 52 are moved axially. As shown in FIG. 13, intermediate gear 58 is attached rotatably to one end of swingable arm 61 the other end of which is attached swingably to frame 50. A detection element 62A of switch 62 abuts on swingable arm 61. Spring 63 is attached to the free end of arm 61 to which intermediate gear 58 is attached so as to bias intermediate gear 58 against gears 57 and 60. Spring 63, switch 62, arm 61 and intermediate gear 58 constitute closure detecting mechanism 64 which detects closure prescribed in JIS (Japanese Industrial Standard) (6.4 in T1635-1986). If syringe 70 is closed for some reason, the movement of movable member 52 is hindered in spite of the operation of motor 59. If closure pressure exceeds an allowable value, a slippage occurs between intermediate gear 58 and gear 60 attached to motor 59, so that intermediate gear 58 moves away from gears 57, 60 against the action of spring 63. Switch 62 detects such movement of intermediate gear 58 and generates a signal which causes a controller (not shown) to stop motor 59.

In order to allow syringe 70 to be replaced, piston 72 must manually be moved freely relative to casing 71. To this end, the syringe pump has a clutch mechanism which transmits the drive force of screw shaft 54 to movable member 52 or releases the transmission of the drive force of screw shaft 54 to movable member 52. In the syringe pump of FIG. 12, the clutch mechanism has a structure in which the pair of half nuts 55 abuts disengageably on screw shaft 54.

Another technique related to a syringe pump is disclosed in Published Unexamined Japanese Utility Model Application Sho 63-190921 in which the syringe pump includes a frame having a mount for a syringe, a lever supported by the frame and fixing the syringe to the mount, a movable member supported movably on the frame for operating the piston in the syringe, a motor attached to the frame, a roller provided on each of an output shaft of the motor, the movable member and the frame, and a wire belt extending around these rollers to move the movable member in accordance with the drive of the motor. If the motor is driven, the wire belt causes the movable member to be driven on the principle of a running block to discharge a liquid from the syringe. The clutch mechanism is attached to the lever such that when the lever is operated, the wire belt is rendered tensile or released to transmit the drive force of the motor to the movable member or render the movable member freely movable.

However, in the syringe pump of FIG. 12, the screw shaft and half nuts each are a precise mechanical part to thereby render the syringe pump expensive, disadvantageously. In order to adjust a replaced syringe minutely, the piston can be moved by an appropriate stroke with the syringe casing being fixed, in which case the half nuts 55 are at any position along screw shaft 54 under which condition the clutch is actuated. Since the position of half nuts 55 relative to screw shaft 54 is not fixed, half nuts 55 and screw shaft 54 may not coincide in thread crest in which case half nuts 55 and screw shaft 54 are not appropriately engaged with each other and can rotate uselessly. Therefore, the position of movable member 52 must manually be adjusted minutely such that half nuts 55 and screw shaft 54 are appropriately engaged with each other. This adjustment is troublesome. Even if half nuts 55 and screw shaft 54 coincide with each other in thread crest and bottom, there may be a backlash between the crests and bottoms, so that there occurs an error between a quantity of drive given by motor 59 and a quantity of movement of movable member 52 and hence an error in a discharged quantity of liquid.

Since the syringe pump of the Application '921 uses the wire belt extending around the roller provided on the motor output shaft to transmit the drive force by the frictional force occurring between the roller and wire belt, there arises a slippage between the wire belt and roller to thereby hinder accurate discharge of liquid disadvantageously. Especially, if the roller rapidly rotates at high speed directly after the actuation of the motor, the roller becomes likely to slip relative to the wire belt due to transition from static friction to dynamic friction. In order to eliminate such slippage, the wire belt is required to be extend around the rollers doubly or triply. In this case, the wire belt would be rubbed by itself and deteriorated in durability.

SUMMARY OF THE INVENTION

It is an object of the present invention to provide a durable syringe pump which has a simple structure to discharge a small quantity of liquid accurately.

In order to achieve the object, the present invention provides a syringe pump which includes a casing for containing a liquid therein and a piston disposed movably in the casing for discharging a liquid, comprising: a frame having a mount for mounting one of the casing and piston thereon; a movable member supported movably on the frame and having the other of the casing and piston attached thereon; a drive mechanism including a motor disposed on the frame, a drive roller attached to an output shaft of the motor, a follower roller attached rotatably on the frame, a transmission member attached to the drive roller and follower roller for transmitting the torque of the drive roller to the follower roller; a drive force converting mechanism including a transmission roller attached rotatably to the movable member for converting the movement of the transmission member to rotation, a transmission gear attached rotatably to the movable member, a speed increasing mechanism disposed between the transmission roller and the transmission gear for increasing the speed of transmission roller and transmitting the increased speed of the transmission roller to the transmission gear; an endless guide member engaged with the transmission gear for guiding the movable member; a clutch mechanism including a rotating member engaged with the guide member and a rotation preventing member disengageably engaging the rotating member for preventing rotation of the rotating member, the rotating member and rotation preventing member having teeth provided on their opposing ends and engaging each other.

The transmission member may include an endless member disposed on the drive roller and follower roller. The endless member may include a timing belt.

A lever may be supported by the frame for fixing one of the casing and piston to the mount. A cam member may be attached to an end of the lever and abutting on the rotation preventing member. Means may be disposed between the rotation preventing means and the frame for biasing the rotation preventing means toward the cam member. The cam face of the cam member is spaced from the center of rotation of the cam member such that when the lever is at a position where the lever fixes one of the casing and piston, the rotation preventing member abuts on the rotating member while when the lever is at a position where the lever releases one of the casing and piston from its fixed state, the rotation preventing member is moved away from the rotating member.

A radially outward extending ear may be formed on the rotation preventing member. A position restricting spring may be disposed between one side of the ear and the frame for restricting the movement of the rotation preventing member in one of opposite circumferential directions. A stop may be fixed to the frame on the opposite side of the ear from the position restricting spring for abutting on the ear. The position restricting spring may be disposed so as to prevent a circumferential movement of the rotation preventing member occurring when the piston moves forward relative to the casing. The frame side end of the position restricting spring is engaged with a bias adjusting bolt screwed into the frame, the bolt being disposed movable axially of the position restricting spring. In addition, in the present invention, a detection switch may be provided for detecting a circumferential movement of the rotation preventing member against the action of the position restricting spring. The detection switch may be connected to a control unit which when the detection switch detects the circumferential movement of the rotation preventing member, the control unit receives a detection signal from the detection switch and delivers to the motor a signal to stop the motor.

The speed increasing mechanism may include a plurality of gears. The guide member may include a timing belt.

In order to discharge a liquid using the syringe according to the present invention, the teeth of the rotational member of the clutch mechanism are engaged with the teeth of its rotation preventing member, namely, the clutch is actuated.

When the motor is operated under such conditions, the drive mechanism which includes the drive roller, passive roller and transmitting member is actuated. The movement of the transmitting member is changed to the rotation of the transmission roller constituting part of the drive force converting mechanism, and the rotation of the roller is then transmitted through an acceleration mechanism to the transmission gear.

The rotation of the transmission gear is transmitted to the guide member which is engaged with the rotating member which is prevented from rotating by the rotation preventing member. Therefore, the guide member is fixed to the frame and the transmission gear moves along the guide member. This causes the transmission gear and the movable member to move to thereby move the piston relative to the casing to cause the syringe to discharge a liquid.

Generally, there is a backlash between the rotation preventing member, rotating member, guide member and transmission gear, which backlash causes an error in the discharge of the liquid. The rotation of the transmission roller of the drive mechanism is accelerated by the acceleration mechanism and then transmitted to the transmission gear, so that the error arising in the transmission gear is reduced on the side of the drive mechanism, and hence the error in the discharge of the liquid due to the backlash is reduced.

In order to replace the syringe after a predetermined liquid discharging operation is ended, the rotating member and rotation preventing member of the clutch mechanism are moved away from each other and hence their engaging teeth are disengaged from each other, namely, the clutch is disengaged. Under such condition, even if the motor is actuated, only the guide member is moved and the movable member is not. Under such conditions, the syringe is removed from the frame mount, the movable member is manually moved to a predetermined position, and a new syringe is placed on the frame mount.

Thereafter, in order to discharge a liquid using the new syringe, the engaging teeth of the rotating member and rotation preventing member are again engaged with each other and the motor is then operated. Even if the crests of the teeth of both members abut on each other, rotation of the rotating member causes the engaging teeth of both the members to change their relative position circumferentially to thereby cause the engaging teeth to engage automatically with each other.

DETAILED DESCRIPTION OF THE PREFERRED EMBODIMENT(S)

One embodiment of the present invention will be described with reference to the drawings.

Figure 1:
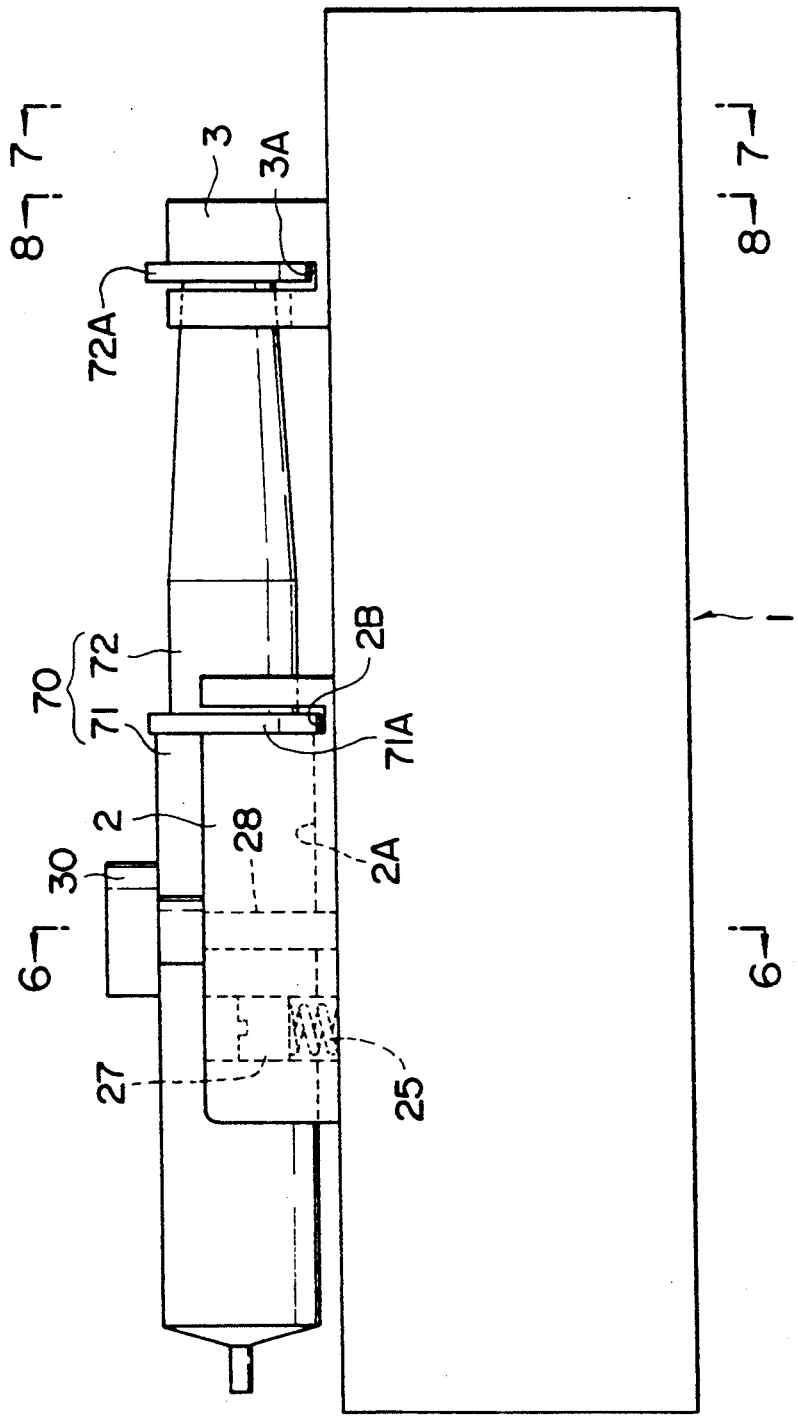
FIG. 1 is a front view of one embodiment of syringe pump according to the present invention.
Figure 2:
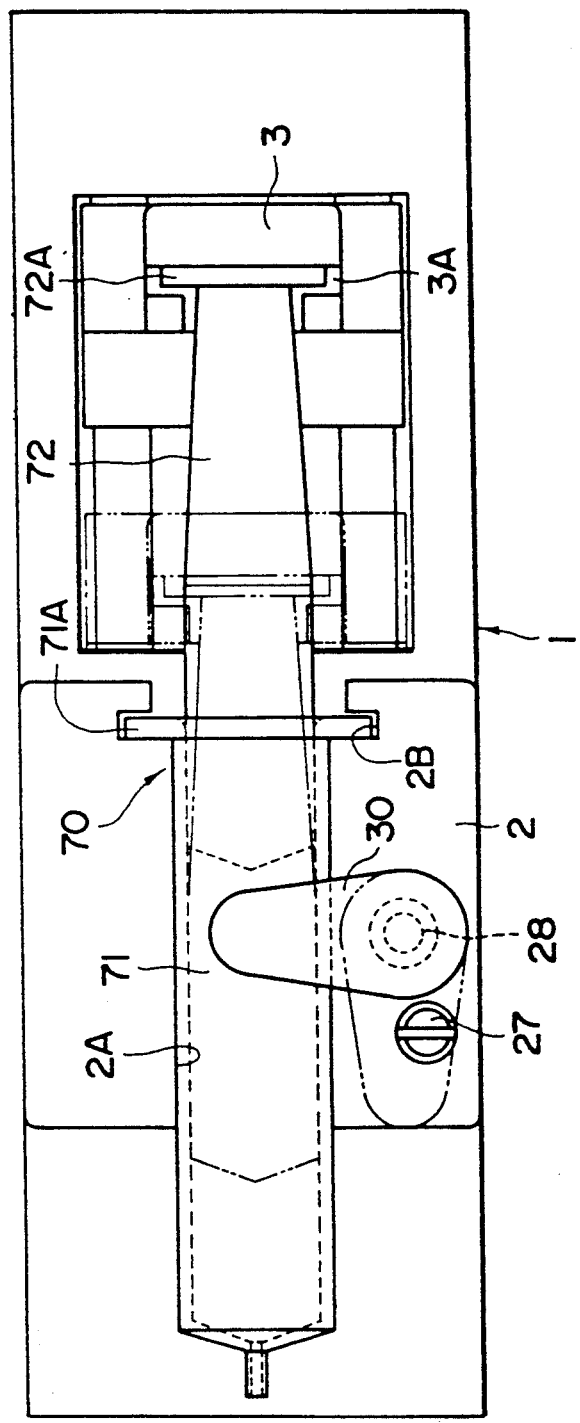
FIG. 2 is a plan view of the embodiment.
Figure 3:
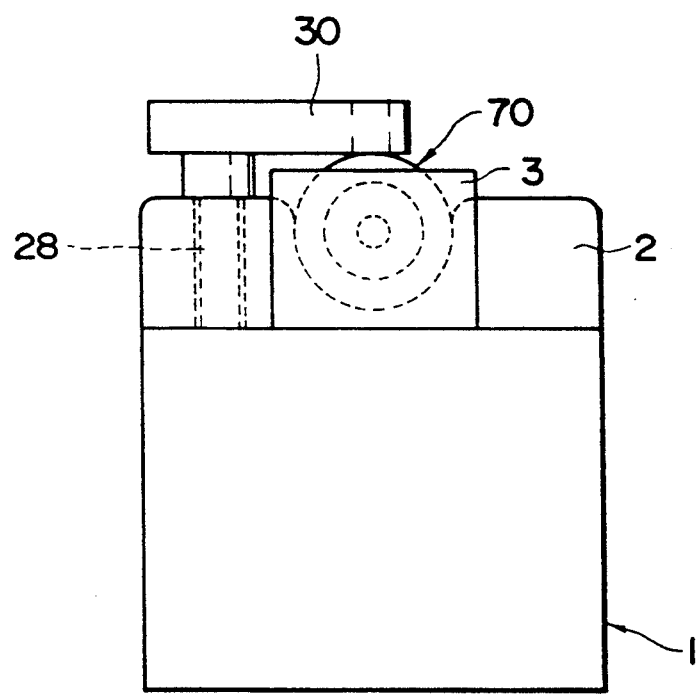
FIG. 3 is a right-hand side view of the embodiment.

FIGS. 1-3 shows the appearance of the embodiment. Syringe pump 70 of the present embodiment includes a cylindrical casing 71 which contains a liquid such as a carcinostatic substance and a piston 72 disposed movably in casing 71. Casing 71 has at an end flange 71A while piston 72 has at an end flange 72A.

Provided on top of an elongated box-like frame 1 in FIGS. 1-3 is mount 2 which mounts casing 71 thereon. Mount 2 has an upper end with U-like groove 2A fitting on casing 71. Mount 2 has groove 2B thereon in the vicinity of the midpoint of frame 1 engaging casing flange 71A. Piston flange 72A is engaged in the groove 3A of movable member 3.

FIGS. 4-9 show the internal structure of the syringe pump. In FIGS. 4-9, a pair of guide rods 4 is disposed within frame 1 so as to parallel to syringe 70. The pair of guide rods 4 supports the central portion of movable member 3 such that the movable member is movable along guide rods 4. Therefore, when movable member 3 moves forward and backward along guide rods 4, piston 72 moves correspondingly relative to casing 71.

Movable member 3 has on its lower end a pair of opposing protrusions 3B across which a pair of parallel shafts 5 is provided perpendicular to guide rods 4. One shaft 5 has at its center first gear 6 attached rotatably thereto. Transmission roller 7 with a plurality of external teeth thereon is fixed coaxially to first gear 6. The other shaft 5 has second gear 8 attached rotatably thereto and engaged with first gear 6. Transmission gear 9 is fixed coaxially to second gear 8. First gear 6 is larger in number of teeth than second gear 8. Gears 6 and 8 constitute speed increasing mechanism 10 which increases the speed of transmission roller 7 and transmits the increased speed to transmission gear 9. Transmission roller 7, transmission gear 9 and speed increasing mechanism 10 constitute drive force transmission mechanism 11.

Motor 12 is attached to one internal side of frame 1 and includes a stepping motor which causes a liquid to be discharged with an accuracy of one pulse in accordance with a motor drive signal. Output shaft 12A of motor 12 is disposed parallel to shafts 5. Drive roller 13 with a plurality of external teeth thereon is attached to output shaft 12A. Shaft 14 is provided parallel to shafts 5 in the vicinity of the other internal side of frame 1 and has follower roller 15 with a plurality of external teeth thereon attached rotatably thereto. First timing belt 16 comprising a transmission member extends around drive roller 13 and follower roller 15 and is engaged with transmission roller 7. Motor 12, drive roller 13, follower roller 15 and first timing belt 16 constitute drive mechanism 17.

Shaft 18 is disposed parallel to shaft 14 between motor 12 and movable member 3 below mount 2 and has rotating member 19 with a plurality of external teeth thereon rotatably attached thereto. Shaft 14 has third gear 20 attached rotatably thereto. Second timing belt 21 as a guide member extends around rotating member 19 and third gear 20. Second timing belt 21 is engaged with transmission gear 9 to thereby guide movable member 3 along a linear path. Rotation preventing member 22 is attached rotatably to shaft 18 and disengageably to rotating member 19, which cooperates with rotation preventing member 22 to constitute a clutch mechanism. Members 19 and 22 have at at opposing ends engaging teeth 19A and 22A, respectively, engaging with each other. Spring 23 is provided as biasing means between a side of frame 1 and the opposite end of rotating preventing member 22 from engaging teeth 22A. It biases rotating preventing member 22 toward rotating member 19 to ensure the engagement of engaging teeth 19A and 22A. Rotation preventing member 22 has a pair of radially outward extending ears 22B and 22C at the spring 23 side end thereof. A lower surface of left-hand ear 22B of FIGS. 4 and 5 abuts on stop 24 fixed to frame 1 while an upper surface of ear 22B is engaged with a lower end of coil spring 25, which biases ear 22B toward stop 24. Namely, rotation preventing member 22 is normally fixed by stop 24 and coil spring 25. Under such condition, if motor output shaft 12A is rotated counterclockwise in FIG. 9, rotating member 19 tries to rotate clockwise, but rotation preventing member 22 prevents rotating member 19 and second timing belt 21 from rotating, so that movable member 3 moves leftward in the figure along timing belt 21 to thereby advance piston 72. If motor output shaft 12A rotates clockwise in FIG. 9, movable member 3 moves rightward to thereby move piston 72 backward.

Figure 4:
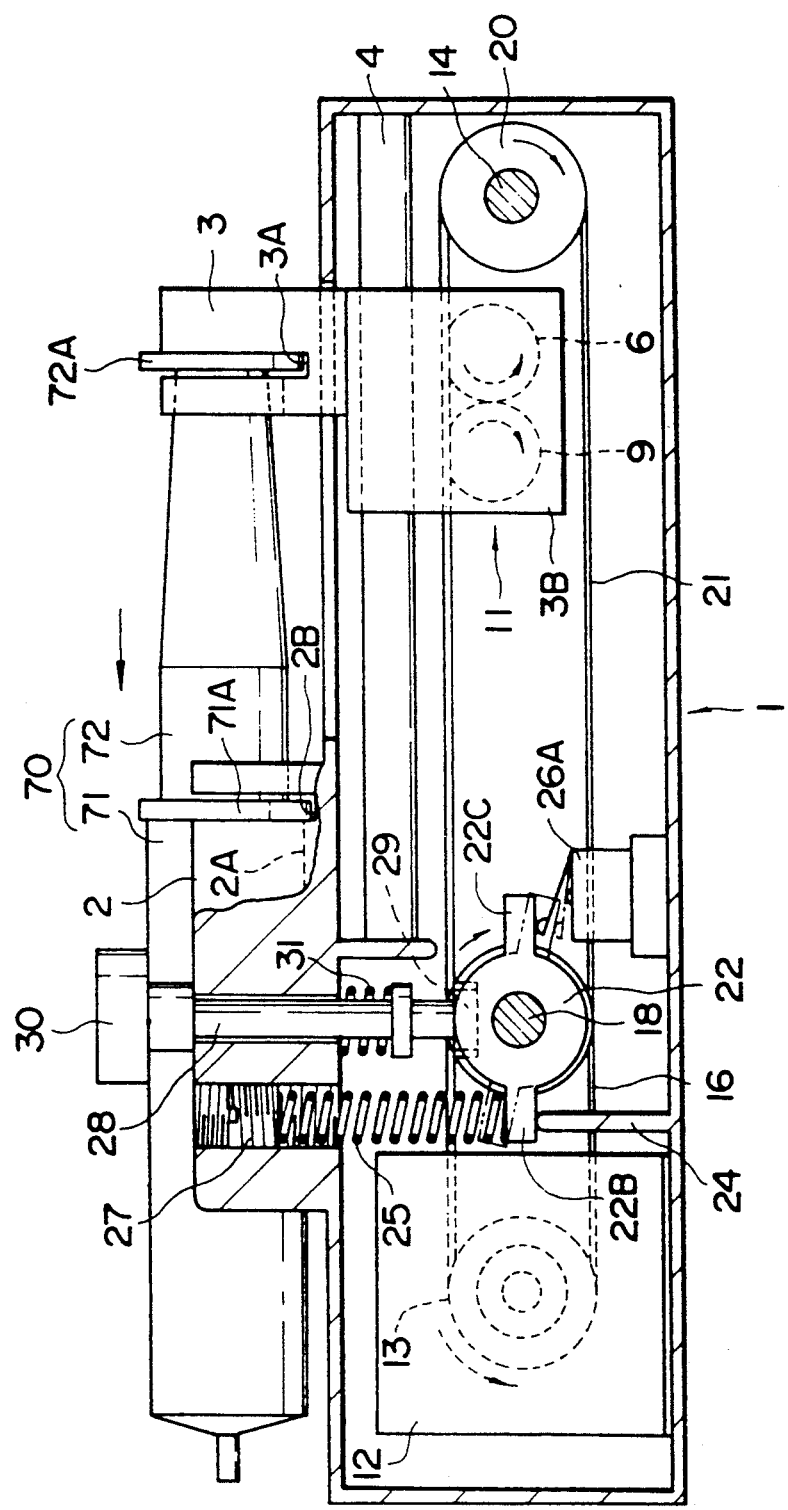
FIG. 4 is a longitudinal cross-sectional view of the embodiment.
Figure 5:
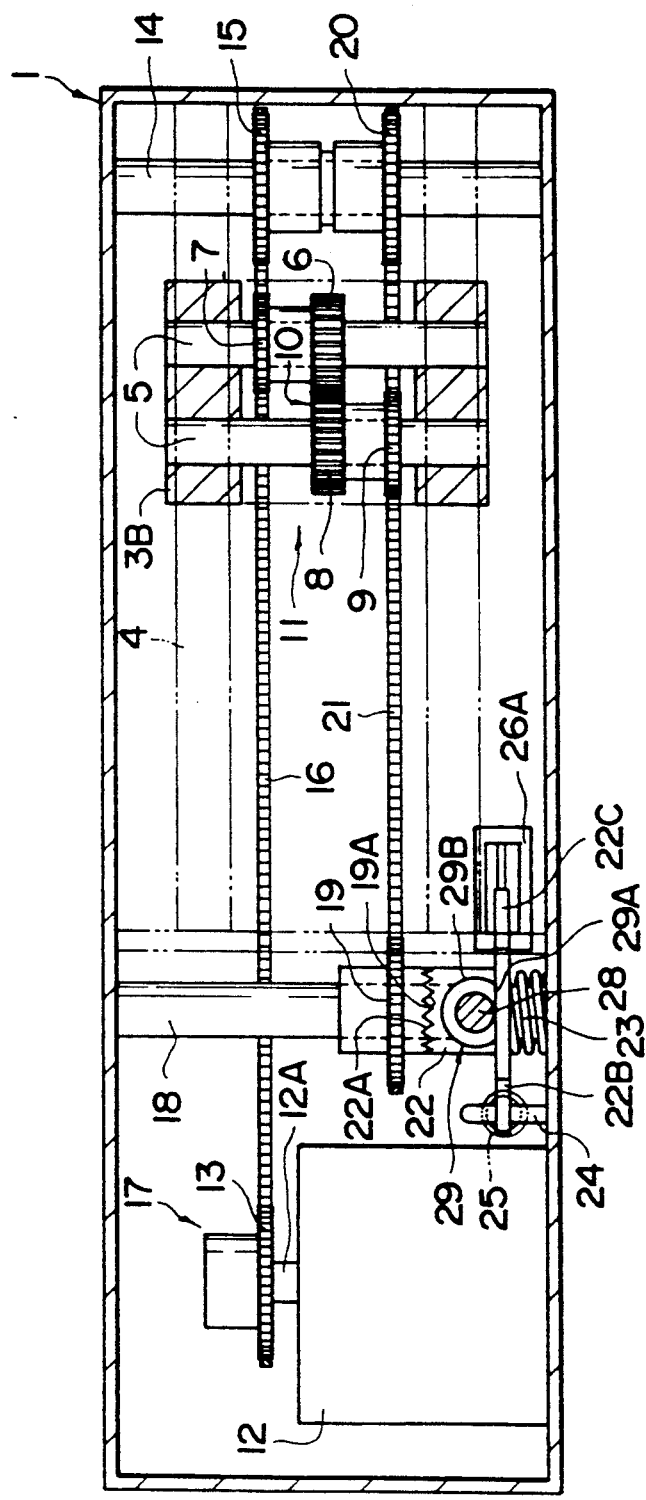
FIG. 5 is a transverse cross-sectional view of the embodiment.
Figure 6:
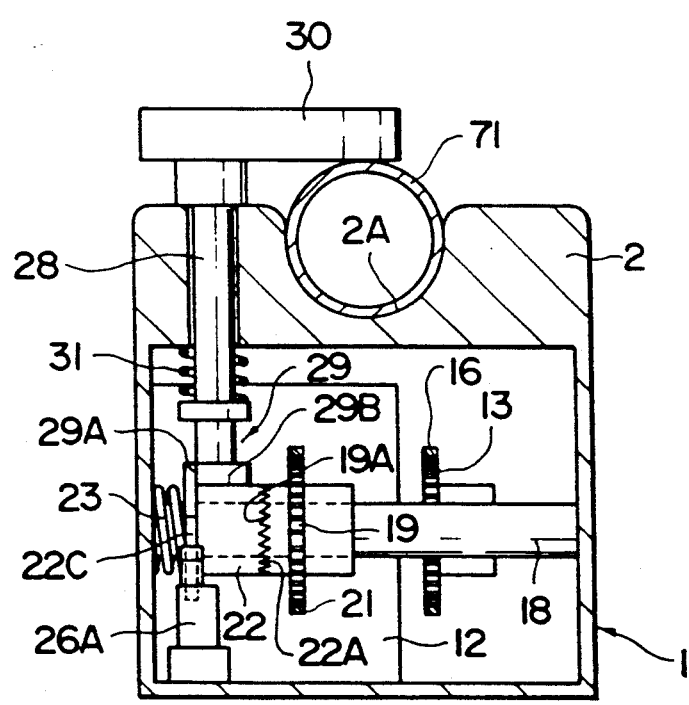
FIG. 6 is a cross-sectional view taken along the line 6—6 of FIG. 1.
Figure 7:
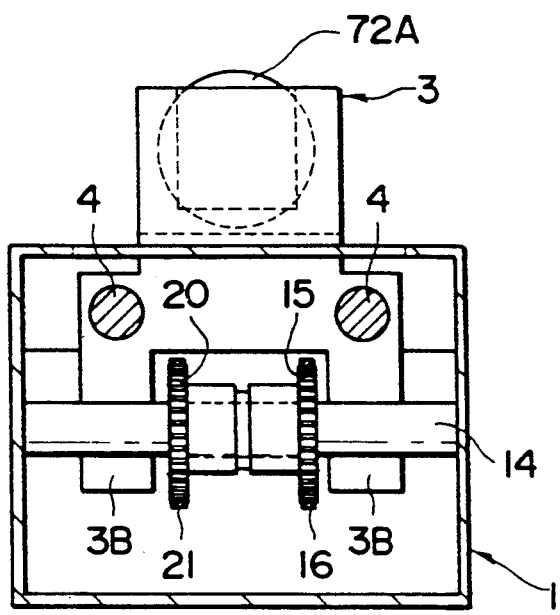
FIG. 7 is a cross-sectional view taken along the line 7—7 of FIG. 1.
Figure 8:
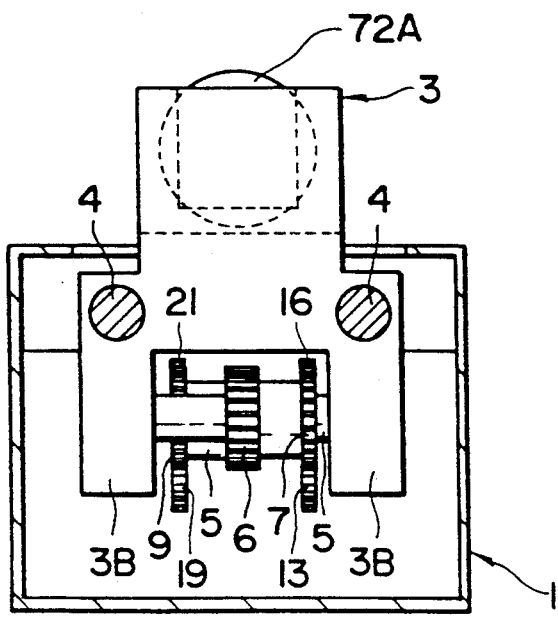
FIG. 8 is a cross-sectional view taken along the line 8—8 of FIG. 1.
Figure 9:
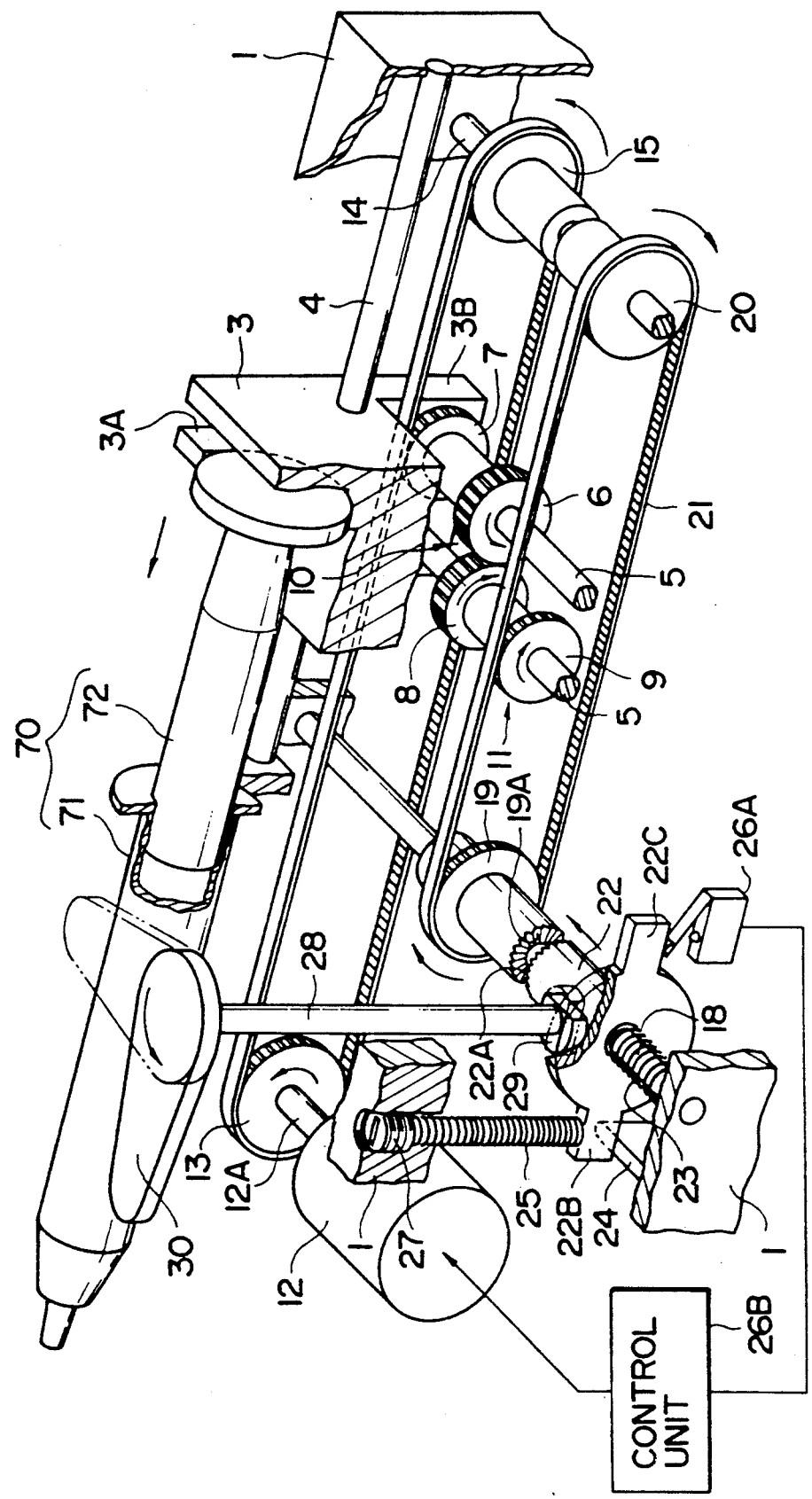
FIG. 9 is a schematic perspective view of the embodiment.

Disposed below right-hand ear 22C in FIGS. 4 and 5 is detection switch 26A which detects closure prescribed in JIS (6.4, T1635-1985). If casing 71 has been closed when piston 72 moves forward, rotation preventing member 22 tries to rotate clockwise against the action of coil spring 25. Detection switch 26A detects such rotation of member 22. Detection switch 26A is connected to control unit 26B, which receives a detection signal from detection switch 26A when same detects the movement of rotation preventing member 22 and sends to motor 12 a signal to stop the operation of the motor. An upper end of coil spring 25 abuts on a lower end of adjusting screw 27 screwed into the upper portion of frame 1. Adjusting screw 27 is movable axially of coil spring 25. By adjusting a quantity of movement of coil spring 25, the biasing force of coil spring 25 and hence a set value of the closure pressure to be sensed is adjusted.

Rod 28 is disposed movable vertically and circumferentially in the upper end of frame 1. Rod 28 has a cam member 29 at a lower end and a syringe hold lever 30 at an upper end. Cam member 29 has a linear cam face 29A and an arc cam face 29B. Linear cam face 29A is spaced from the cam rotation center such that when syringe hold lever 30 is at a position where syringe casing 71 is fixed, rotation preventing member 22 abuts on rotating member 19. Arc cam face 29B is spaced from the center of rotation of the cam member such that when syringe hold lever 30 is at a position where casing 71 is released from its fixed state, rotation preventing member 22 is away from rotating member 19. Spring 31 is provided between the upper surface of cam member 29 and an upper end of frame 1 so as to urge syringe hold lever 30 and hence casing 71 downward.

In operation, in order to cause syringe 70 to discharge a liquid, engaging teeth 19A and 20A of rotating member 19 and rotation preventing member 22 of the clutch mechanism are engaged with each other or the clutch is engaged.

Under such condition, if motor 12 is operated, drive mechanism 17 comprising drive roller 13, passive roller 15 and first timing belt 16 is actuated. The movement of first timing belt 16 is converted to rotation of transmission roller 7 constituting a part of drive force converting mechanism 11 and this rotation is transmitted to transmission gear 9 through speed increasing mechanism 10 comprising two gears 6 and 8.

Rotation of transmission gear 9 is intended to be transmitted to second timing belt 21 and rotating member 19. However, rotating member 19 is prevented from rotating by rotation preventing member 22. Therefore, second timing belt 21 is fixed to frame 1 and transmission gear 9 moves along second timing belt 21 and hence movable member 3 also moves back and forth along guide rod 4. Piston 72 engaged with movable member 3 is then moved back and forth relative to casing 71 engaged with mount 2 to thereby cause syringe 70 to discharge a liquid.

Generally, there is a backlash among rotation preventing member 22, rotating member 19, second timing belt 21 and transmission gear 9. However, the rotational speed of transmission roller 7 is increased by speed increasing mechanism 10 and then transmitted to transmission gear 9, so that an error occurring in transmission gear 9 is reduced on the side of drive mechanism 17.

When an abnormal pressure exceeding a set value occurs within casing 71 in the liquid discharging operation, rotation preventing member 22 rotates clockwise in FIG. 4 against the action of coil spring 25. Detection switch 26A detects such rotation to thereby cause control unit 26B to stop motor 12.

Figure 10A:
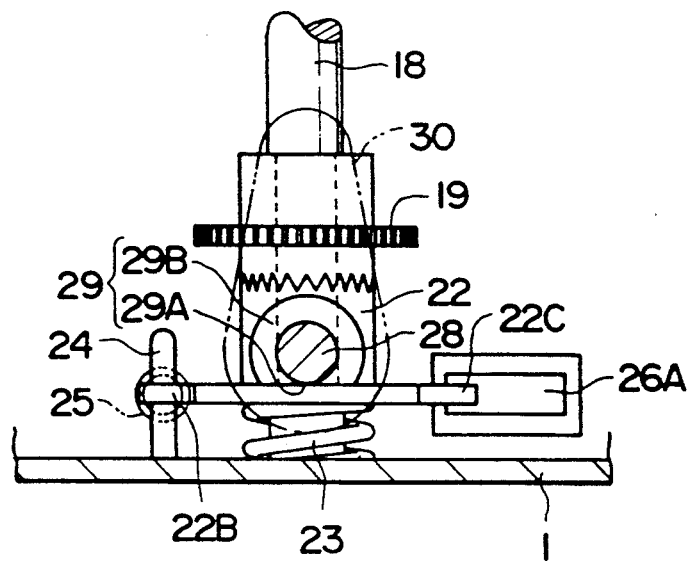
FIGS. 10(A) and 10(B) each are a plan view of a clutch mechanism.
Figure 10B:
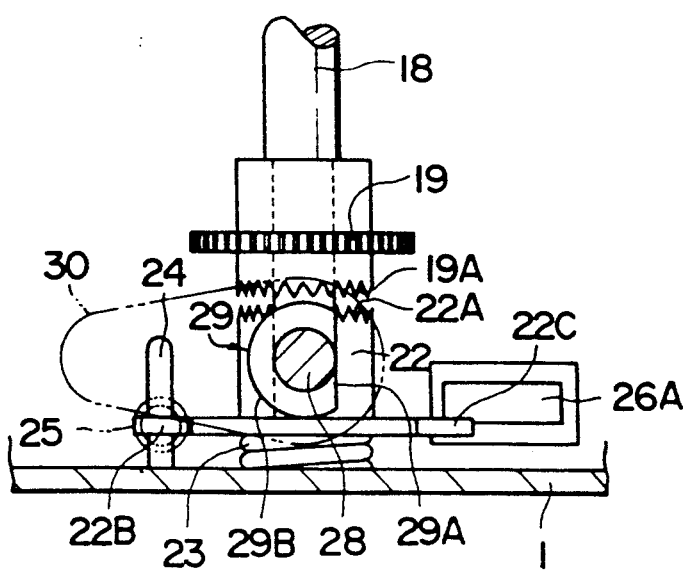

In order to exchange syringe 70 after a predetermined liquid discharging operation is ended, syringe hold lever 30 is rotated until it aligns with the longitudinal axis of frame 1. Cam member 29 also rotates in accordance with rotation of lever 30 and arc cam face 29B abuts on rotation preventing member 22, as shown in FIG. 10(B) by which operation rotation preventing member 22 is moved away from rotating member 19 to disengage engaging teeth 19A and 22A from each other and hence the clutch is disengaged. Under such condition, rotating member 19 only rotates and movable member 3 will not move even if motor 12 is operated.

When the clutch is disengaged, movable member 3 is manually moved to an appropriate position such that syringe 70 is insertable between mount 2 and movable member 3. Under such condition, syringe casing 71 is inserted into U-like groove 2A in mount 2 and flange 71A of piston 72 is engaged in groove 3B in movable member 3.

Thereafter, lever 30 is turned through 90 degrees to fix same to mount 2 of casing 71. Cam member 29 is also rotated in accordance with the turning of lever 30 and linear cam face 29A abuts on rotation preventing member 22. Thus, as shown in FIG. 10(A), rotation preventing member 22 abuts on rotating member 19 and hence engaging portions 19A and 16A are engaged with each other and hence the clutch is engaged.

Thereafter, in order to cause replaced new syringe 70 to discharge a liquid, motor 12 is again operated. Even if the crests of engaging teeth 19A and 22A of both members 19 and 22 abut on each other and the clutch is not completely engaged, the operation of motor 12 causes rotating member 19 to rotate to thereby change the relative circumferential position of engaging teeth 19A and 22 of both the members 19 and 22 and hence to cause these teeth to automatically engage each other.

According to such structure of the present embodiment, the clutch mechanism is composed of rotating member 19 and rotation preventing member 22 with engaging teeth 19A and 22A, respectively, so that the operation of motor 12 causes teeth 19A and 22A to automatically engage each other and rotating member 19 will not rotate uselessly relative to rotation preventing member 22. In addition, since speed increasing mechanism 10 which increases the speed of transmission roller 7 and transmits the increased speed to transmission gear 9 is disposed in drive force converting mechanism 11, an error transmitted to transmission gear 9 is reduced even if there is a play between members 19 and 22 due to backlash between engaging teeth 19A and 22A, etc. The error can be made to approach 0 limitlessly by adjusting the speed increase rate of speed increasing mechanism 10. Provision of a clutch on motor output shaft 12A would be conceivable. However, according to such structure, a possible error arising in the clutch would be transmitted to transmission gear 9 intactly or in an amplified manner. Therefore, in the present embodiment, a liquid is discharged accurately with syringe 70.

Since drive mechanism 17, drive force transmission mechanism 11 and the guide member are constituted by a plurality of gears and timing belts to drive movable member 3 in the present embodiment, the present embodiment produces the following advantages. Since the use of the screw shaft and nuts is eliminated, the cost of the syringe pump is reduced. In addition, no wire belt is used and hence the durability of the syringe pump is improved.

Figure 12:
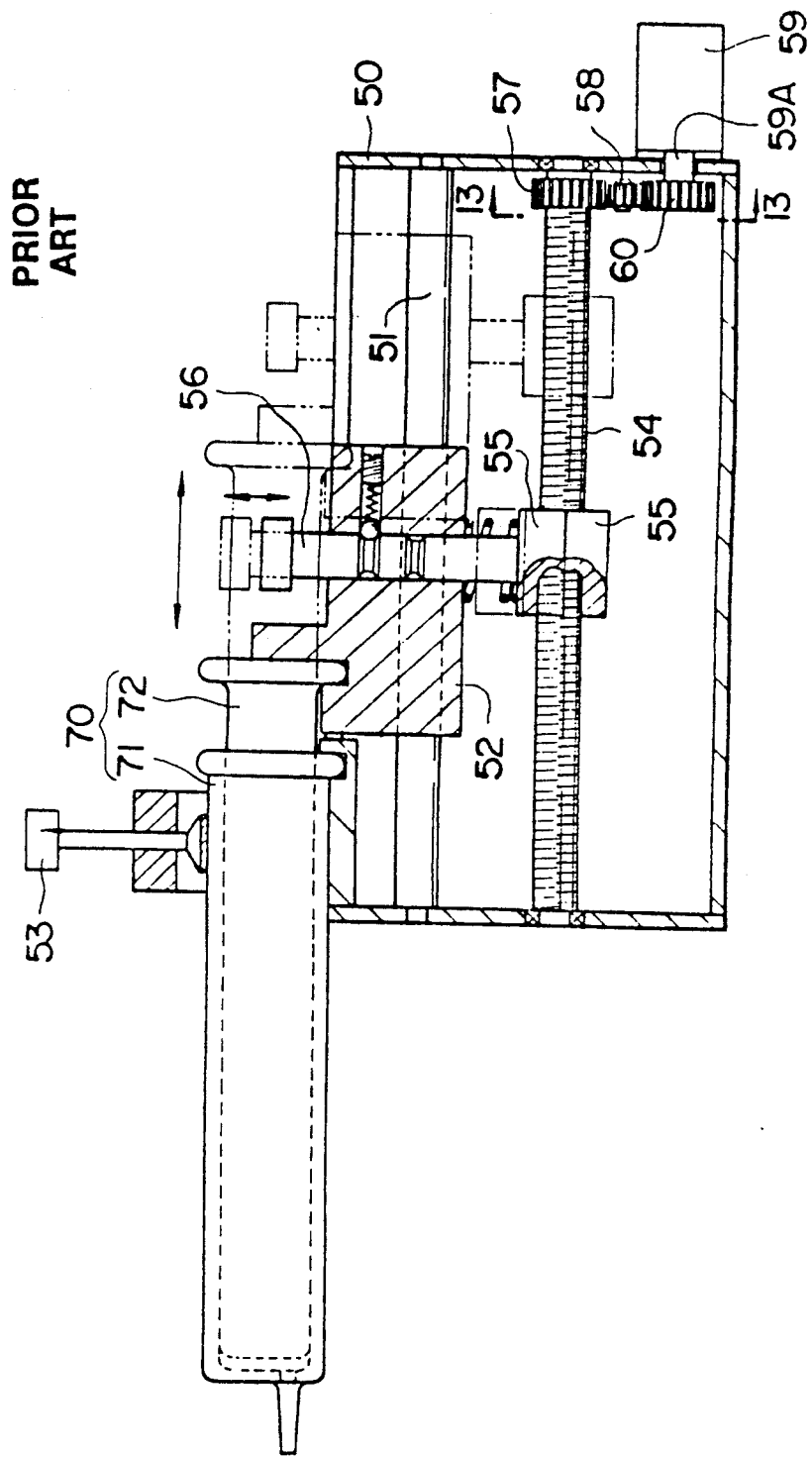
FIG. 12 is a longitudinal cross-sectional view of a syringe pump of the art related to the present invention.
Figure 13:
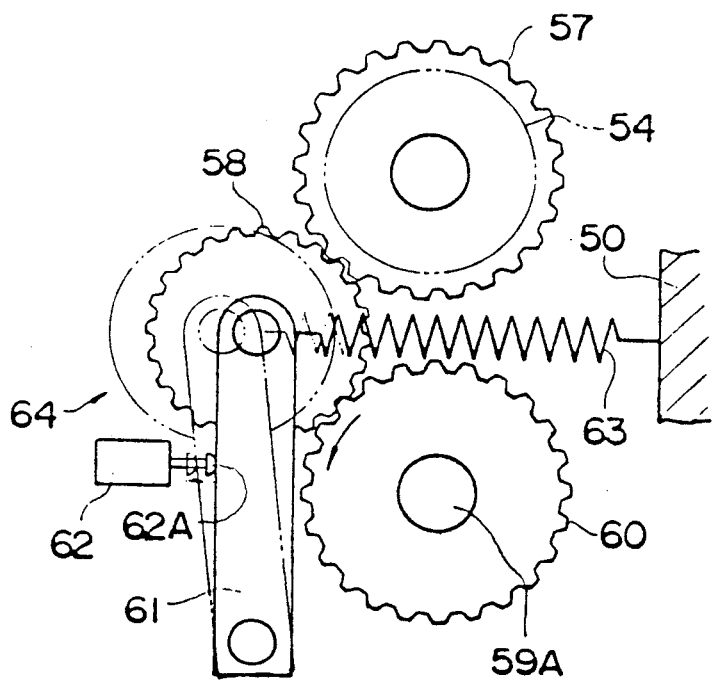
FIG. 13 is a cross-sectional view taken along the line 13—13 of FIG. 12.

In the present embodiment, closure of syringe 70 prescribed in JIS is detected accurately irrespective of the kind of the syringe pump. When syringe 70 is closed in closure detection mechanism 64 shown in FIGs. 12 and 13, gear 60 slides relative to intermediate gear 58, which moves away from other gears 57 and 60 against the action of spring 63. The force of intermediate gear 58 to move against the action of spring 63 is influenced by the slide surface of the gear or the finished state of the curved gear tooth face. However, the degree of curved tooth face finish varies from one gear to another, so that the force of intermediate gear 58 to move differs from one syringe pump to another. In contrast, the closure detection mechanism in the present embodiment is arranged such that stop 24 and position restricting spring 25 are disposed in opposed relationship with respect to rotation preventing member 22 and that detection switch 26A is disposed which detects the rotation of rotation preventing member 22 against the action of position restricting spring 25. Therefore, the closure in syringe 70 is detected without using slippage between the gears, so that closure in syringe 70 can be detected irrespective of the kind of the syringe pump used. In addition, provision of control unit 26B in the present embodiment causes the discharging of a liquid by syringe 70 to be automatically stopped. Since the end of position restricting spring 25 is engaged with bias adjusting screw 27 screwed into frame 1. adjustment of a quantity of movement of bias adjusting screw 27 causes the biasing force of spring 25 and hence the set value of closure pressure to be detected to be changed.

Since cam member 29 with linear cam face 29A and arc cam face 29B is attached at the end of lever 30. turning lever 30 to remove and attach syringe 70 causes the clutch mechanism to operate automatically. Therefore, syringe 70 can be replaced rapidly and easily.

Figure 11:
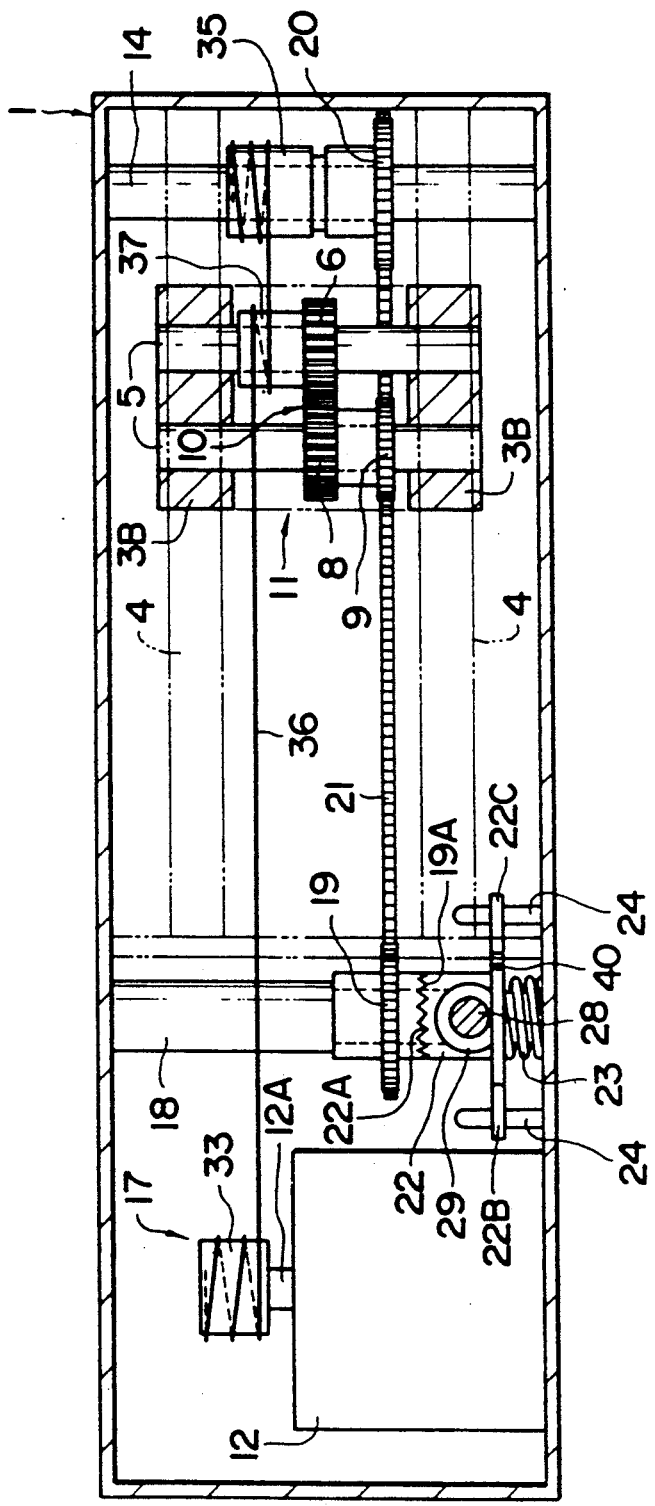
FIG. 11 is a transverse cross-sectional view of a modification of the present invention.

While in the above embodiment the transmission member is illustrated as including timing belt 16. and roller 13. passive roller 15 and transmission roller 7 are illustrated in the form of a gear, the transmission member may be replaced with a chain, and drive roller 13, and passive roller 15 and transmission roller 7 may take the form of a sprocket structure. As shown in FIG. 11, the transmission member may be wire belt 36, and drive roller 13 and passive roller 15 each may be a cylindrical member to which an end of wire belt 36 is attached, and transmission roller 37 may be a cylindrical member around which the middle portion of wire belt 36 extends. If a timing belt is used as the transmission member as in the previous embodiment. it is ensured that the drive of motor 12 is transmitted to speed increasing mechanism 10.

The mechanism for detecting closure in syringe 70 may have a structure shown in FIG. 11 in which stops 24 abut on corresponding ears 22B and 22C of rotation preventing member 22. a distortion gage 40 which detects pressure exerted on rotation preventing member 22 when rotation member 22 rotates is attached to righthand ear 22C in FIG. 11. and motor 12 is stopped by a control unit (not shown) when distortion gage 40 detects a pressure exceeding a predetermined value.

Alternatively, rotating member 19 and rotation preventing member 22 may be attached to shaft 14 and third gear 20 may be attached to gear 18.

Motor 12 is not necessarily required to be a stepping motor, but may be a third motor such as a pulse motor or a regular motor. Preferably, a motor the speed of which is controlled is used.

Piston 72 and casing 71 may be attached to mount 2 and movable member 3, respectively.

A plurality of syringes 70 may be mounted on the pump in which case all the syringes may be attached on mount 2 and single movable member 3. Alternatively, a plurality of movable members 3 may be used to which corresponding syringes are attached and driven separately.

As described above, the inventive syringe pump has a simple durable structure to permit an accurate small quantity of liquid to be discharged.

What is claimed is:

1. A syringe pump which includes a casing for containing liquid therein and a piston disposed movably in the casing for discharging a liquid, comprising:
a frame having a mount for mounting one of the casing and piston thereon;
a movable member supported movably on said frame and having the other of the casing and piston attachable thereon;
a drive mechanism including a motor disposed on said frame, a drive roller attached to an output shaft of said motor, a follower roller attached rotatably on said frame, a transmission member attached to said drive roller and follower roller for transmitting the torque of said drive roller to said follower roller;
a drive force converting mechanism including a transmission roller attached rotatably to said movable member for converting the movement of said transmission member to rotation, a transmission gear attached rotatably to said movable member, a speed increasing mechanism disposed between said transmission roller and said transmission gear for increasing the speed of transmission roller and transmitting the increased speed of said transmission roller to said transmission gear;
an endless guide member engaged with said transmission gear for guiding said movable member;
a clutch mechanism including a rotating member engaged with said guide member and a rotation preventing member disengageably engaging said rotating member for preventing rotation of said rotating member, the rotating member and rotation preventing member having teeth provided on facing ends thereof and engaging each other.

2. A syringe pump according to claim 1, wherein said transmission member includes an endless member disposed on said drive roller and follower roller.

3. A syringe pump according to claim 2, wherein said endless member includes a timing belt.

4. A syringe pump according to claim 1, comprising a lever supported by said frame for fixing one of said casing and piston to said mount, a cam member having a cam face attached to an end of said lever and abutting on said rotation preventing member, means disposed between said rotation preventing means and said frame for biasing said rotation preventing means toward said cam member, and wherein the cam face of said cam member is spaced from the center of rotation of said cam member such that when said lever is at a position where said lever fixes one of said casing and piston, said rotation preventing member abuts on said rotating member while when said lever is at a position where said lever releases one of said casing and piston from its fixed state, said rotation preventing member is moved away from said rotating member.

5. A syringe pump according to claim 1, comprising a radially outward extending ear formed on said rotation preventing member, a position restricting spring disposed between one side of said ear and said frame for restricting the movement of said rotation preventing member in one of opposite circumferential directions, and a stop fixed to said frame on the opposite side of said ear from said position restricting spring for abutting on said ear.

6. A syringe pump according to claim 5, wherein said position restricting spring is disposed so as to prevent a circumferential movement of said rotation preventing member occurring when said piston moves forward relative to said casing.

7. A syringe pump according to claim 6, wherein an end of said spring adjacent said frame is engaged with a bias adjusting screw screwed into said frame, the screw being disposed movable axially of said position restricting spring.

8. A syringe pump according to claim 7, comprising a detection switch for detecting a circumferential movement of said rotation preventing member against the action of said position restricting spring.

9. A syringe pump according to claim 8, wherein said detection switch is connected to a control unit which when said detection switch detects the circumferential movement of said rotation preventing member, the control unit receives a detection signal from said detection switch and delivers to said motor a signal to stop said motor.

10. A syringe pump according to claim 1, wherein said speed increasing mechanism includes a plurality of gears.

11. A syringe pump according to claim 1, wherein said guide member includes a timing belt.

* * * * *